(12) United States Patent
Yaguchi et al.

(10) Patent No.: US 7,563,242 B2
(45) Date of Patent: Jul. 21, 2009

(54) ULTRASONIC SURGERY APPARATUS

(75) Inventors: Shigeo Yaguchi, Ota-ku (JP); Hidenori Kanda, Okazaki (JP)

(73) Assignee: Nidek Co., Ltd. (JP)

( * ) Notice: Subject to any disclaimer, the term of this patent is extended or adjusted under 35 U.S.C. 154(b) by 767 days.

(21) Appl. No.: 10/874,262

(22) Filed: Jun. 24, 2004

(65) Prior Publication Data

US 2004/0267136 A1 Dec. 30, 2004

(30) Foreign Application Priority Data

Jun. 25, 2003 (JP) .............................. 2003-181583

(51) Int. Cl.
*A61M 3/00* (2006.01)

(52) U.S. Cl. .............................. 604/43; 604/22; 604/35; 604/37; 604/118; 604/289; 604/294; 600/459; 600/466; 600/471; 601/2; 601/14; 601/37; 601/41; 606/159; 606/161; 606/169; 606/170; 606/171

(58) Field of Classification Search .................... 604/19, 604/22, 35, 118, 289, 294, 37; 600/459, 600/466, 471; 601/2, 14, 37, 41; 606/159, 606/161, 169–171, 204.25
See application file for complete search history.

(56) References Cited

U.S. PATENT DOCUMENTS

| 5,279,547 | A | * | 1/1994 | Costin | .......................... | 604/22 |
|---|---|---|---|---|---|---|
| 5,591,127 | A | | 1/1997 | Barwick, Jr. et al. | | |
| 5,700,240 | A | | 12/1997 | Barwick, Jr. et al. | | |
| 5,800,424 | A | | 9/1998 | Sumiya | | |
| 6,275,718 | B1 | | 8/2001 | Lempert | | |
| 7,377,645 | B2 | | 5/2008 | Wrobel et al. | | |

FOREIGN PATENT DOCUMENTS

| EP | 0-945 732 A | 9/1999 |
|---|---|---|
| JP | H09-313496 | 7/1992 |
| JP | 9-508298 | 8/1997 |
| JP | H06-506125 | 12/1997 |
| JP | 11-206803 | 8/1999 |

OTHER PUBLICATIONS

JPO - Notice of Rejection; Application No.: 2003-181583, dated Oct. 11, 2007.

* cited by examiner

*Primary Examiner*—Nicholas D Lucchesi
*Assistant Examiner*—Quynh-Nhu H Vu
(74) *Attorney, Agent, or Firm*—Rader Fishman & Grauer PLLC; Ronald P. Kananen (57) ABSTRACT

An ultrasonic surgery apparatus capable of setting surgical conditions properly in accordance with hardness of a nucleus lentis and performing surgery with efficiency is disclosed. The ultrasonic surgery apparatus includes an ultrasonic vibration inducing unit, having an ultrasonic chip which induces ultrasonic vibrations to fragment and emulsify a nucleus lentis, an input unit which inputs a judgment result of hardness of the nucleus lentis, and a setting unit which sets a condition of the ultrasonic vibrations thereafter based on the inputted judgment result.

8 Claims, 6 Drawing Sheets

```
 0 ≦ Maximum US power ≦ 10% → Grade 2.5 or less
10 < Maximum US power ≦ 20% → Grade 3.0
20 < Maximum US power ≦ 30% → Grade 3.5
30 < Maximum US power ≦ 40% → Grade 4.0 or more
              ( US time≦30 seconds→Grade 4.0     )
              ( US time>30 seconds→Grade 4.5 or more )
```

FIG. 5

|  | Maximum US power |
|---|---|
| Grade 2.5 or less | 10% |
| Grade 3.0 | 20% |
| Grade 3.5 | 30% |
| Grade 4.0 | 40% |
| Grade 4.5 or more | 60% |

FIG. 6A

|  | Maximum US power | Pulse-duty ratio |
|---|---|---|
| Grade 2.5 or less | 20% | 30% |
| Grade 3.0 | 25% | 40% |
| Grade 3.5 | 30% | 40% |
| Grade 4.0 | 35% | 40% |
| Grade 4.5 or more | 40% | 50% |

| | Hardness | Maximum US power |
|---|---|---|
| $\frac{R}{R+G+B} < 40\%$ | Soft | 30% |
| $40\% \leq \frac{R}{R+G+B} \leq 45\%$ | Normal | 40% |
| $45\% < \frac{R}{R+G+B}$ | Hard | 50% |

FIG. 9

ULTRASONIC SURGERY APPARATUS

BACKGROUND OF THE INVENTION

1. Field of the Invention

The present invention relates to an ultrasonic surgery apparatus to be used in cataract surgery in which an opaque nucleus lentis (nucleus of a crystalline lens) caused by a cataract is subjected to ultrasonic vibrations so as to fragment and emulsify the nucleus lentis, and then the emulsified nucleus lentis is aspirated and removed so as to discharge the nucleus lentis.

2. Description of Related Art

In cataract surgery, an ultrasonic surgery apparatus is known which gives (applies) ultrasonic vibrations to a nucleus lentis using a tubular ultrasonic chip (referred to as an US chip, hereinafter) attached to a handpiece so as to fragment and emulsify the nucleus lentis, and aspirates and removes the emulsified nucleus lentis with an irrigation liquid supplied inside an eye so as to discharge the nucleus lentis. In this kind of apparatus, surgical conditions such as power (output) of the ultrasonic vibrations given to the US chip (referred to as US power, hereinafter), a pulse-duty ratio of the US power (the ratio of oscillation to intermission of the US power), and aspiration pressure are set by a switch or the like.

Hardness of the nucleus lentis differs according to the age of a patient, the progress of a cataract and the like, and individual differences exist between patients. However, conventionally, the surgery is generally performed under the same surgical conditions regardless of the hardness of the nucleus lentis. In addition, for dealing with the difference in the hardness of the nucleus lentis, the US power is controlled by depression operation of a pedal of a footswitch. Though the setting of the surgical conditions such as the US power and the pulse-duty ratio is changeable in accordance with the hardness of the nucleus lentis, judgment of the hardness of the nucleus lentis greatly depends on experience of a surgeon and is also troublesome.

SUMMARY OF THE INVENTION

An object of the invention is to overcome the problems described above and to provide an ultrasonic surgery apparatus capable of setting surgical conditions properly in accordance with hardness of a nucleus lentis and performing surgery with efficiency.

To achieve the objects and in accordance with the purpose of the present invention, an ultrasonic surgery apparatus has an ultrasonic vibration inducing unit, having an ultrasonic chip, which induces ultrasonic vibrations to fragment and emulsify a nucleus lentis, an input unit which inputs a judgment result of hardness of the nucleus lentis, and a setting unit which sets a condition of the ultrasonic vibrations thereafter based on the inputted judgment result.

In another aspect of the present invention, an ultrasonic surgery apparatus has an ultrasonic vibration inducing unit having an ultrasonic chip which induces ultrasonic vibrations to fragment and emulsify a nucleus lentis, an aspirating unit which aspirates the emulsified nucleus lentis, a judging unit which judges hardness of the nucleus lentis, and a setting unit which sets at least one of power, a pulse-duty ratio and the number of pulses of the ultrasonic vibrations thereafter, and aspiration pressure and a rate of aspiration flow of the aspiration unit, based on a judgment result.

Additional objects and advantages of the invention are set forth in the description which follows, are obvious from the description, or may be learned by practicing the invention. The objects and advantages of the invention may be realized and attained by the ultrasonic surgery apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
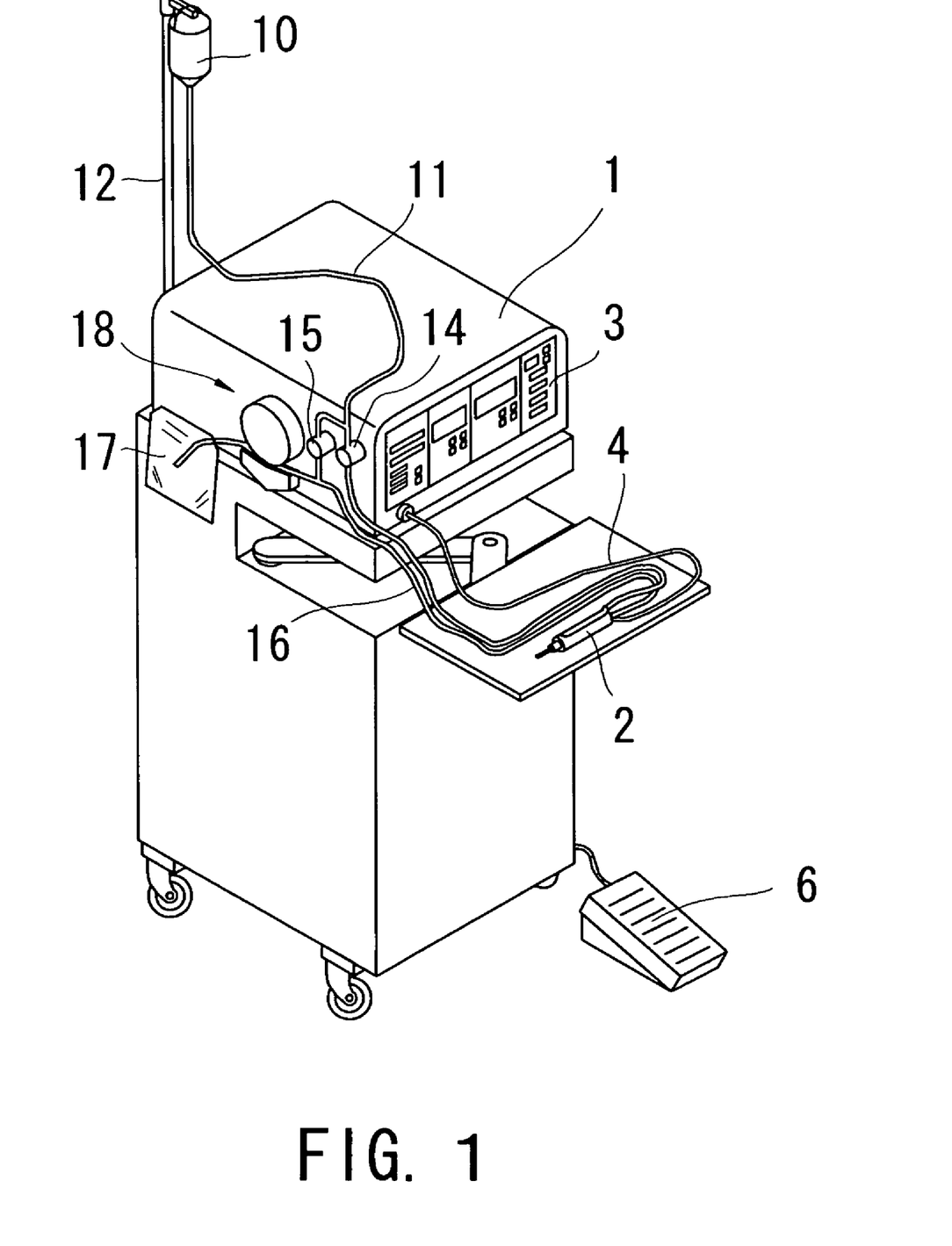
FIG. 1 is a schematic external view of an ultrasonic surgery apparatus.
Figure 2:
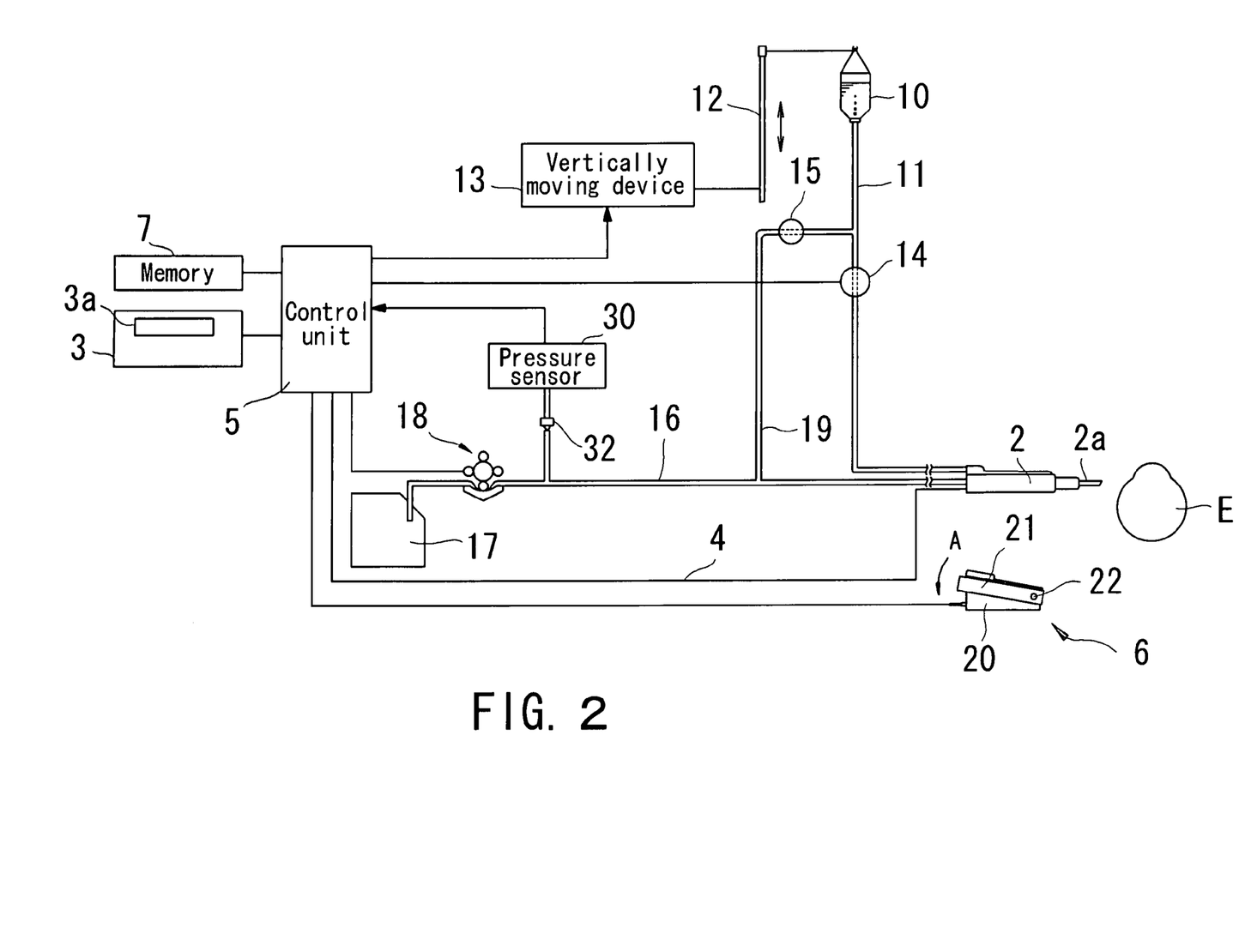
FIG. 2 is a view showing a schematic configuration of the ultrasonic surgery apparatus.

A detailed description of one preferred embodiment of an ultrasonic surgery apparatus embodied by the present invention is provided below with reference to the accompanying drawings. FIG. 1 is a schematic external view of an ultrasonic surgery apparatus. FIG. 2 is a view showing a schematic configuration of the apparatus.

A main body 1 of the apparatus stores a control unit 5 which controls and drives the entire apparatus. An ultrasonic handpiece (referred to as an US handpiece, hereinafter) 2 for surgery is held by a surgeon, and a tubular US chip 2a having an aspiration hole is attached to a tip of the US handpiece 2. Ultrasonic vibrations generated by a vibrator in the US handpiece 2 is amplified and conveyed to the US chip 2a. The US chip 2a thereby becomes capable of giving (applying) ultrasonic vibrations to a nucleus lentis so as to fragment and emulsify the nucleus lentis. The vibrator in the US handpiece 2 is provided with driving energy from the control unit 5 in the main body 1 via a cable 4. For the ultrasonic vibrations conveyed to the US chip 2a, a continuous oscillation or a pulse oscillation may be selected, and a mode-changing switch in an input unit (operation panel) 3 may be used to switch to a mode for either oscillation.

Further, the input unit 3 is provided with a group of switches for individually setting various surgical conditions such as irrigation pressure, aspiration pressure, a rate of aspiration flow, US power and a pulse-duty ratio, a display part 3a for displaying information about the setting, information notified to the surgeon and the like, and others. Additionally, the mode-changing switch includes a switch for switching between an US1 mode and an US2 mode described later. The control unit 5 is connected with a memory 7.

An irrigation bottle 10, filled with an irrigation liquid such as a saline which is supplied to a patient's eye E, is hung on a pole 12. The pole 12 is moved vertically by a vertically moving device 13 or can be moved manually, so that the height of the bottle 10 may be changed. The height of the bottle 10 is set so as to properly maintain pressure inside the eye E. A control valve 14 is provided midway along an irrigation tube 11 for leading the irrigation liquid to the eye E, and is opened and closed for flow control of the irrigation liquid. One end of the irrigation tube 11 is connected to the bottle 10 and the other end is connected to the US handpiece 2.

An aspiration tube 16 is used to discharge a waste liquid containing the supplied irrigation liquid and the emulsified nucleus lentis which are aspirated through the aspiration hole of the US chip 2a into a drainage bag 17. Provided midway along the aspiration tube 16 are a connecting part 32 connected to a pressure sensor 30, and a peristaltic aspiration pump 18. Further, the aspiration tube 16 communicates with the irrigation tube 11 via a bypass tube 19, and a control valve 15 is opened and closed for flow control through the bypass tube 19. The aspiration pressure inside the aspiration tube 16 is always detected by the pressure sensor 30. When the aspiration pressure reaches a predetermined (preset) upper limit, the control unit 5 controls to stop the aspiration pump 18. Additionally, in a case where the aspiration pressure should be lowered, the control unit 5 controls to open the control valve 15, and the irrigation liquid is permitted to flow from the irrigation tube 11 via the bypass tube 19 into the aspiration tube 16 for lowering the aspiration pressure. An upper limit value of the aspiration pressure (the maximum aspiration pressure) is set by the switch in the input unit 3.

Figure 3:
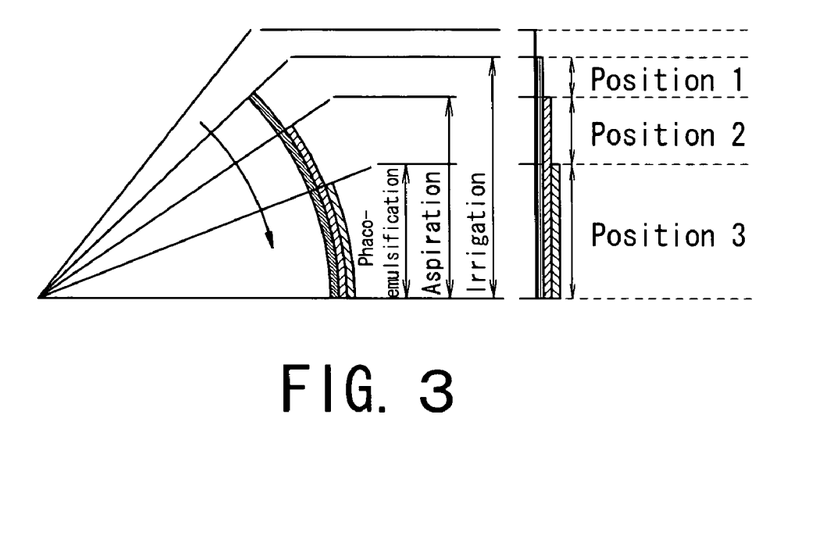
FIG. 3 is a view illustrating a relation of a depression amount (depression position) of a footswitch to each operation of irrigation, aspiration and phacoemulsification.

A footswitch 6 is used for controlling each operation of irrigation, aspiration and phacoemulsification (ultrasonic vibrations) of the apparatus in accordance with a depression amount (depression position) of a pedal 21. A rear part of the pedal 21 (a right side of FIG. 2) is coupled to a base part 20 via a shaft 22, and the pedal 21 is rotatable in a direction of the arrow A shown in FIG. 2 about the shaft 22. And, each operation of irrigation, aspiration and phacoemulsification (ultrasonic vibrations) is controlled in response to a signal of the depression amount (depression position) of the pedal 21 of the footswitch 6 (see FIG. 3). In addition, in a position 3 with which phacoemulsification is performed (i.e., irrigation and aspiration are also performed), the US power is arranged to change linearly in accordance with the depression amount (depression position) of the pedal 21. A maximum value of the US power (the maximum US power) when the pedal 21 is depressed at the maximum is set by the switch in the input unit 3.

Next, operation of the apparatus as above will be described. Here, in a method of surgery in which the nucleus lentis is fragmented (split) and emulsified, and then aspirated, an example will be explained where the hardness of the nucleus lentis is judged based on data about the ultrasonic vibrations induced (applied) in an initial stage at the time of the fragmentation of the nucleus lentis and the surgical conditions thereafter are determined (set) based on results thereof.

Firstly, the operation mode of the apparatus in the initial stage of the surgery is put into the US1 mode by the switch in the input unit 3. In the US1 mode, the hardness of the nucleus lentis is detected and judged. When the US1 mode is set, the control unit 5 calls up the surgical conditions to be used as a standard, which are previously stored in the memory 7, and performs setting. For example, each setting is performed such that the aspiration pressure is 20 kPa (150 mmHg), the aspiration flow rate is 26 mL/min, the US power is 40%, the number of US pulses (the number of pulses per second) is 60 pps, and the pulse-duty ratio is 40%. Incidentally, the set value of the US power here is the maximum US power. The set values of the respective standard surgical conditions are displayed on the display part 3a. Additionally, the set values of the respective standard surgical conditions may also be changed respectively by the switch in the input unit 3.

Figure 4:
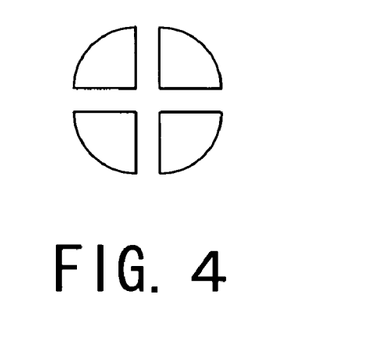
FIG. 4 is a view illustrating a state in which a nucleus lentis is fragmented (split) in an initial stage of surgery.

When the preparation of the apparatus is completed, the surgeon inserts the US chip 2a inside a crystalline capsule while observing the eye E through a microscope unit. Then, the pedal 21 of the footswitch 6 is depressed to the position 3, and the ultrasonic vibrations are induced in addition to supply and aspiration of the irrigation liquid. By inducing the ultrasonic vibrations, in the initial stage of the surgery, the nucleus lentis is fragmented (split) as shown in FIG. 4. Incidentally, not only a four-part split but also a two-part split, an eight-part split or the like may be available. When the fragmentation of the nucleus lentis is completed to some degree, the operation mode is switched to the US2 mode by the switch in the input unit 3. The control unit 5, regarding the switching signal to the US2 mode as a trigger, judges the hardness of the nucleus lentis based on data about the maximum US power used in the US1 mode and US time (time during which the ultrasonic vibrations are used).

Figure 5:
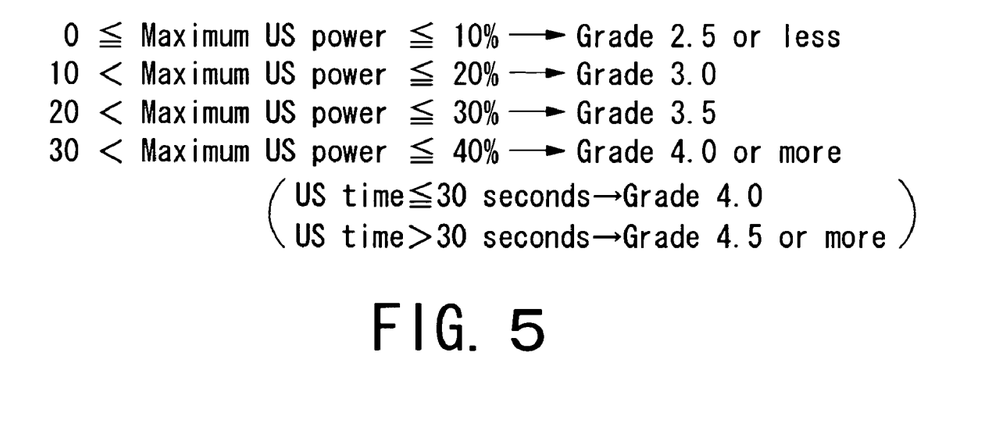
FIG. 5 is a view illustrating an example of judging hardness of the nucleus lentis based on the maximum US power used in an US1 mode.

The hardness of the nucleus lentis is generally graded into five levels of Grade 1 to Grade 5 in descending order of softness (there is another case where grading is performed in 0.5 steps to include Grade 2.5 and the like) In this embodiment, based on the data about the maximum US power and the like in the US1 mode, the hardness of the nucleus lentis is judged as described below (see FIG. 5). Specifically, if the maximum US power in the US1 mode is less than or equal to 10%, the judgment shows Grade 2.5 or less, if the maximum US power is more than 10% and less than or equal to 20%, the judgment shows Grade 3.0, if the maximum US power is more than 20% and less than or equal to 30%, the judgment shows Grade 3.5, and if the maximum US power is more than 30% and less than or equal to 40%, the judgment shows Grade 4.0 or more. Further, in a case where the judgment shows Grade 4.0 or more, Grade 4.0 is shown if the US time is 30 seconds or shorter, and Grade 4.5 or more is shown if the US time is longer than 30 seconds. Incidentally, these values are merely shown as examples.

Besides, the hardness of the nucleus lentis may be judged not only from the maximum US power as mentioned above but also from the mean value or the sum of the US power in the US1 mode.

Figure 6A:
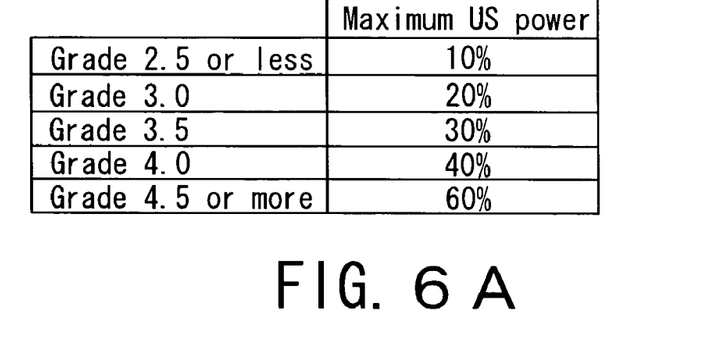
FIGS. 6A and 6B are views illustrating examples in which set values of the maximum US power and a pulse-duty ratio are determined (set) based on the hardness of the nucleus lentis.

The control unit 5 determines (sets) the surgical conditions for the US2 mode based on the judged hardness of the nucleus lentis. FIG. 6A shows an example where the set value of the maximum US power is changed based on the hardness of the nucleus lentis. This setting is performed such that, if the hardness of the nucleus lentis is Grade 2.5 or less, the maximum US power is 10%, if Grade 3.0, the maximum US power is 20%, if Grade 3.5, the maximum US power is 30%, if Grade 4.0, the maximum US power is 40%, and if Grade 4.5 or more, the maximum US power is 60%, respectively. When the setting is performed as above, the judgment result of the hardness of the nucleus lentis and the set surgical conditions are displayed on the display part 3a. The surgeon thereby can confirm the judgment result of the hardness of the nucleus lentis and the surgical conditions determined (set) in accordance with the hardness. Additionally, in this case, the surgical conditions may be respectively changed by the switch in the input unit 3.

Figure 6B:
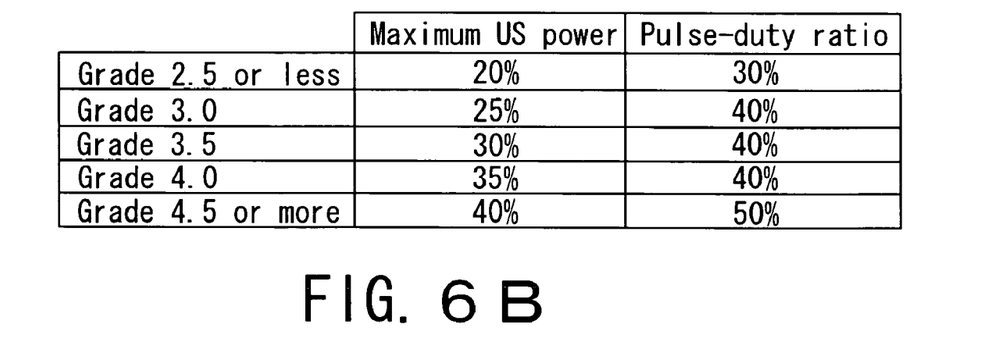

FIG. 6B shows an example where the respective set values of the maximum US power and the pulse-duty ratio are changed based on the hardness of the nucleus lentis. As for the maximum US power and the pulse-duty ratio, the set values are increased with the hardness of the nucleus lentis. More specifically, as for the pulse-duty ratio, the ratio of oscillation is increased with the hardness of the nucleus lentis.

Further, in addition to the US power and the pulse-duty ratio, the set values of the surgical conditions such as the number of pulses, the aspiration pressure and the aspiration flow rate may also be changeable. That is, as for the number of pulses, the set value is increased with the hardness of the nucleus lentis. Also for the aspiration pressure and the aspiration flow rate, each set value is increased with the hardness of the nucleus lentis. Additionally, if the set values of the aspiration pressure and the aspiration flow rate are increased, in order to reduce surge (instability of an anterior chamber) the irrigation pressure (the height of the bottle) is preferably increased accordingly.

As mentioned above, when switched to the US2 mode, the surgical conditions such as the US power conforming to the hardness of the nucleus lentis detected and judged at the time of the US1 mode are automatically set. Therefore, the surgery thereafter may be performed with efficiency without inducing redundant ultrasonic vibrations. Additionally, as the ultrasonic vibrations are not induced more than necessary, complications such as thermal burn may be suppressed.

Figure 7:
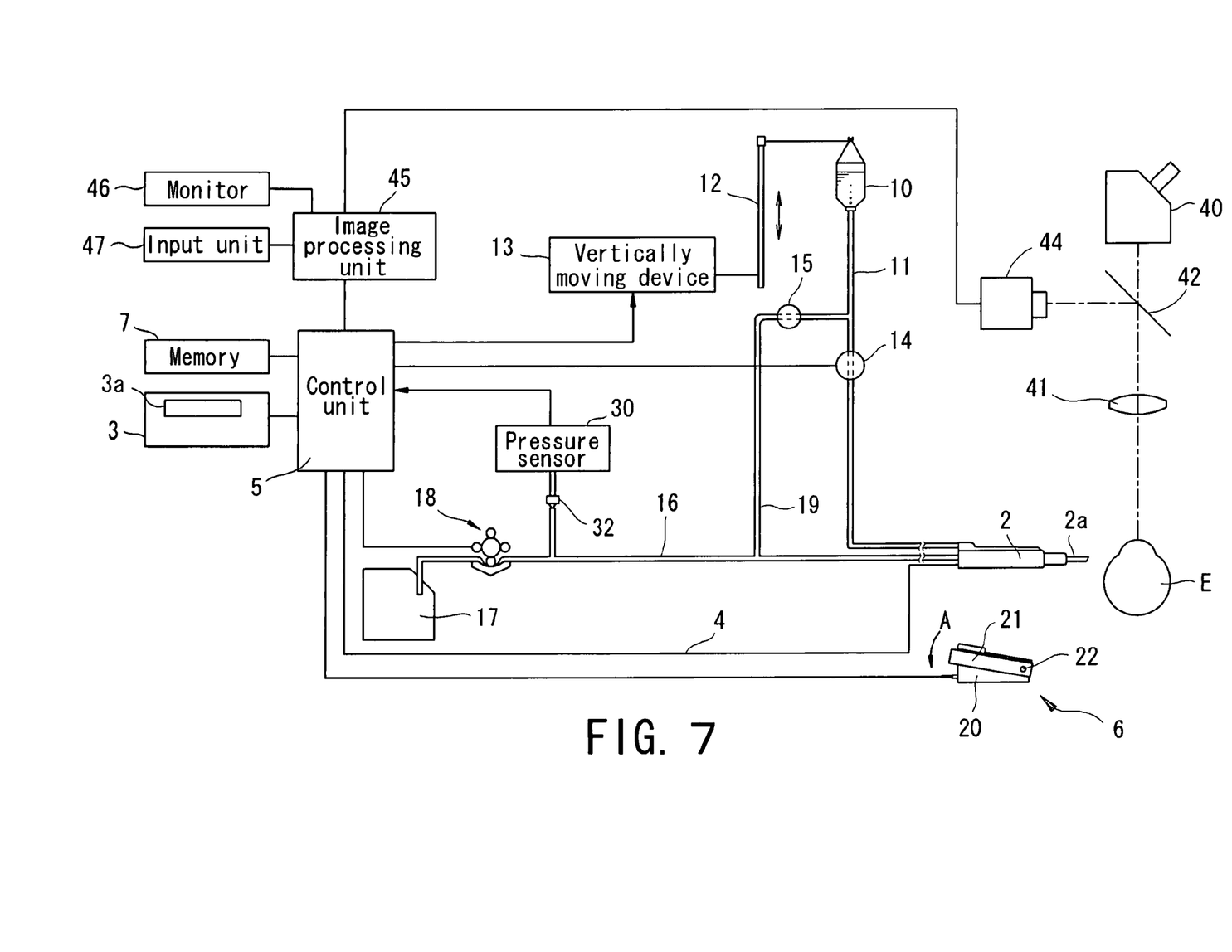
FIG. 7 shows an example of an apparatus for detecting and judging the hardness of the nucleus lentis based on a color of the nucleus lentis.

FIG. 7 shows an example of an apparatus for detecting and judging the hardness of the nucleus lentis based on a color of the nucleus lentis. Elements having the same function as in FIG. 2 are indicated with the same reference numerals.

In FIG. 7, reference numeral 40 indicates a binocular microscope unit of a surgical microscope. 41 is an objective lens of the microscope. A half mirror 42 is arranged in one of binocular optical paths of the microscope unit 40. Arranged in a reflecting direction of the half mirror 42 is an image-pickup unit such as a CCD camera 44 having sensitivity to a visible range. An image of the crystalline lens of the eye E illuminated by an unillustrated illumination light source is picked up by the camera 44. An output from the camera 44 is inputted to an image processing unit 45. A color monitor 46 and an input unit 47 such as a mouse and a keyboard are connected to the image processing unit 45, and the image processing unit 45 is connected to the control unit 5. A personal computer may be utilized as these image processing unit 45 and input unit 47. Besides, the function of the image processing unit 45 may be provided by the control unit 5 contained in the main body 1 of the apparatus. In addition, the camera 44 maybe arranged anywhere such that the image of the crystalline lens can be picked up.

Figure 8:
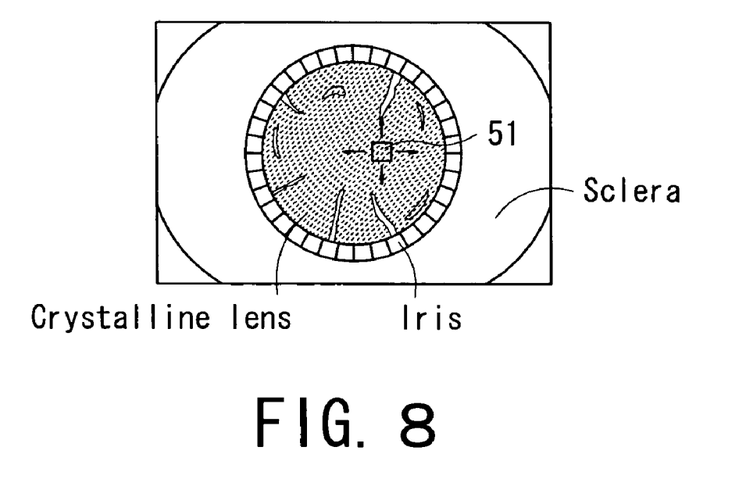
FIG. 8 is a view showing an example of an image of a patient's eye displayed on a monitor.

In the apparatus with such constitution, the surgeon observes the crystalline lens of the eye E through the microscope unit 40 and captures an image of the eye E picked up by the camera 44 into an image memory in the image processing unit 45 according to instruction from the input unit 47. The captured image of the eye E is displayed on the monitor 46 as shown in FIG. 8. The surgeon positions a specifying range 51 for color analysis at an opaque part of the crystalline lens on the image of the eye E displayed on the monitor 46 using the input unit 47 to implement color analysis.

The judgment of the hardness of the nucleus lentis based on a color of the nucleus lentis will be described. It is known that, if the nucleus lentis developing a cataract is milky-white, it is soft, and if the nucleus lentis developing a cataract is brown, it is hard. Thus, the image processing unit 45 analyzes the ratio of R to R (a red component)+G (a green component)+B (a blue component) (i.e., R/(R+G+B)) within the specifying range 51, and judges the hardness of the nucleus lentis based on its analysis result.

Figure 9:
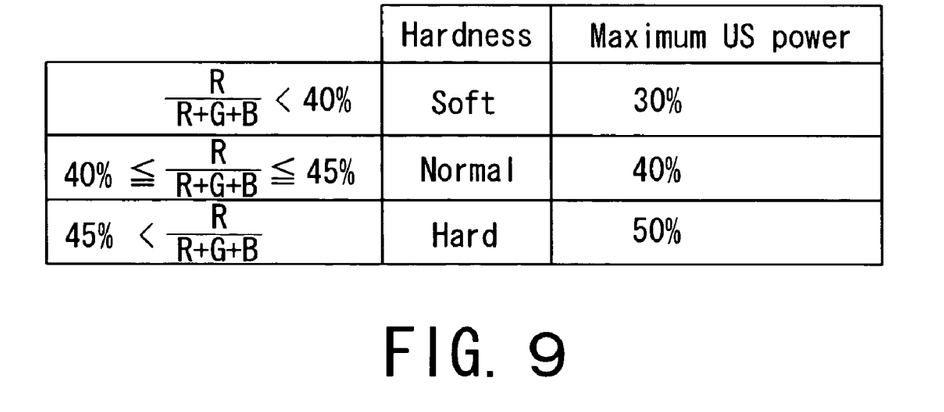
FIG. 9 is a view showing judgment of the hardness of the nucleus lentis according to R/(R+G+B) and the maximum US power determined based on the hardness of the nucleus lentis.

FIG. 9 is a view showing the judgment of the hardness of the nucleus lentis according to R/(R+G+B) and the maximum US power determined based on the hardness of the nucleus lentis. Here, the hardness of the nucleus lentis is graded into three levels of "Soft", "Normal" and "Hard". If R/(R+G+B) is below 40%, the ratio of red is small and the judgment shows "Soft". If R/(R+G+B) is from 40% to 45% inclusive, the judgment shows "Normal". If R/(R+G+B) is above 45%; the ratio of red is large and the judgment shows "Hard". Incidentally, these numerical values are merely shown as examples.

The judgment result of the hardness of the nucleus lentis is inputted to the control unit 5 (the judgment of the hardness of the nucleus lentis may be performed by the control unit 5). The control unit 5 sets the maximum US power based on the judged hardness of the nucleus lentis. The maximum US power is set to be 30% if the judgment shows "Soft", 40% if the judgment shows "Normal", and 50% if the judgment shows "Hard", respectively. This setting information is stored in the memory 7. Further, when the US2 mode is selected, the stored information is called up from the memory 7 and the surgical conditions are automatically set.

Incidentally, by displaying the hardness of the nucleus lentis judged by the image processing unit 45 on the monitor 46 for notifying to the surgeon, even without such constitution that the judgment result is automatically inputted to the control unit 5 as mentioned above, the surgeon can confirm the judgment result of the hardness of the nucleus lentis displayed on the monitor 46 and input by the switch in the input unit 3. In this case, the control unit 5 and the image processing unit 45 are not necessarily connected.

In addition, as the judgment result of the hardness of the nucleus lentis and the set surgical conditions are displayed on the display part 3a, the surgeon can confirm the relation between the hardness of the nucleus lentis and the set surgical conditions, and further can change the setting.

Besides, as in the case of the apparatus with the constitution in FIG. 2, the apparatus may be configured so that at least one of the US power, the pulse-duty ratio, the number of US pulses, the aspiration pressure and the aspiration flow rate is determined (set).

In addition, another constitution may be employed such that the surgeon judges the hardness of the nucleus lentis based on the color of the image of the crystalline lens displayed on the monitor 46 or the image of the crystalline lens observed through the microscope unit 40 and inputs its judgment result by the switch in the input unit 3. In this case, if a color sample and the like indicating color-coding of the hardness of the nucleus lentis is previously prepared, the judgment is performed with ease. Then, the information on the hardness of the nucleus lentis is inputted, and the surgical conditions are set by the control unit 5.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ultrasonic surgery apparatus comprising:
an ultrasonic vibration inducing unit, having a handpiece to a tip of which an ultrasonic chip is attached, which induces ultrasonic vibrations to a nucleus lentis of a patient's eye so as to split, and fragment and emulsify the nucleus lentis;
an irrigating/aspirating unit which leads an irrigation liquid to the eye and discharges a waste liquid out of the eye;
an input unit, having a foot pedal for changing ultrasonic power in response to a depression amount of the foot pedal, which inputs operation signals of the irrigating/aspirating unit and the ultrasonic vibration inducing unit;
an image-pickup unit which picks up an image of a crystalline lens of the eye;
an image processing unit which detects a color of the nucleus lentis by processing an image signal from the image-pickup unit;
a detecting unit which detects hardness of the nucleus lentis based on the detected color of the nucleus lentis; and
a setting unit which automatically sets at least one of a maximum value, a pulse-duty ratio and the number of pulses per unit of time of the ultrasonic power based on a result of the detection by the detecting unit.

2. The ultrasonic surgery apparatus according to claim 1, wherein the detecting unit detects the hardness of the nucleus lentis based on a ratio of a red component in the detected color of the nucleus lentis.

3. The ultrasonic surgery apparatus according to claim 1, wherein the setting unit automatically sets at least one of aspiration pressure and a rate of aspiration flow of the irrigating/aspirating unit based on a result of the detection by the detecting unit.

4. An ultrasonic surgery apparatus comprising:
an ultrasonic vibration inducing unit, having a handpiece to a tip of which an ultrasonic chip is attached, which induces ultrasonic vibrations to a nucleus lentis of a patient's eye so as to split, and fragment and emulsify the nucleus lentis;
an irrigating/aspirating unit which leads an irrigation liquid to the eye and discharges a waste liquid out of the eye;
an input unit, having a foot pedal for changing ultrasonic power in response to a depression amount of the foot pedal, which inputs operation signals of the irrigating/aspirating unit and the ultrasonic vibration inducing unit;
mode setting means which switches between a first mode for detecting hardness of the nucleus lentis and a second mode for fragmenting and emulsifying the nucleus lentis;
a detecting unit which detects the hardness of the nucleus lentis based on a value of the ultrasonic power actually used in response to the actual depression amount of the foot pedal in the first mode; and
a setting unit which automatically sets at least one of a maximum value, a pulse-duty ratio and the number of pulses per unit of time of the ultrasonic power in the second mode, based on a result of the detection by the detecting unit.

5. The ultrasonic surgery apparatus according to claim 4, wherein the setting unit automatically sets at least one of aspiration pressure and a rate of aspiration flow of the irrigating/aspirating unit in the second mode based on a result of the detection by the detecting unit.

6. The ultrasonic surgery apparatus according to claim 1 further comprising a display unit which displays the picked up image of the crystalline lens.

7. An ultrasonic surgery apparatus comprising:
an ultrasonic vibration inducing unit, having a handpiece to a tip of which an ultrasonic chip is attached, which induces ultrasonic vibrations to a nucleus lentis of a patient's eye so as to split, and fragment and emulsify the nucleus lentis;
an irrigating/aspirating unit which leads an irrigation liquid to the eye and discharges a waste liquid out of the eye;
an input unit, having a foot pedal for changing ultrasonic power in response to a depression amount of the foot pedal, which inputs operation signals of the irrigating/aspirating unit and the ultrasonic vibration inducing unit;
a memory which stores an initial value of a maximum value of the ultrasonic power;
mode setting means which switches between a first mode for detecting hardness of the nucleus lentis and a second mode for fragmenting and emulsifying the nucleus lentis;
surgical condition setting means which reads and sets the initial value stored in the memory when the first mode is set; and
a detecting unit which detects the hardness of the nucleus lentis based on a value of the ultrasonic power actually used in response to the actual depression amount of the foot pedal in the first mode, wherein
the surgical condition setting means changes the maximum power of the ultrasonic power from the set initial value based on a result of the detection by the detecting unit when the second mode is set.

8. The ultrasonic surgery apparatus according to claim 7, wherein,
the memory stores initial values of aspiration pressure and a rate of aspiration flow of the irrigating/aspirating unit, and
the surgical condition setting means changes at least one of the aspiration pressure and the rate of aspiration flow from the set initial value based on the result of the detection by the detecting unit when the second mode is set.

* * * * *